(12) United States Patent
Hsieh et al.

(10) Patent No.: US 7,187,750 B1
(45) Date of Patent: Mar. 6, 2007

(54) METHOD AND APPARATUS FOR COMPENSATING NON-UNIFORM DETECTOR COLLIMATOR PLATES

(75) Inventors: Jiang Hsieh, Brookfield, WI (US); Erdogan O. Gurmen, Shorewood, WI (US); Aziz Ikhlef, Waukesha, WI (US); Bing Shen, Apex, NC (US); Gregory Scott Zeman, Waukesha, WI (US); Matthew Aaron Halsmer, Waukesha, WI (US); Tyler Justin Sprenger, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/230,847

(22) Filed: Sep. 20, 2005

(51) Int. Cl.
*A61B 6/03* (2006.01)
(52) U.S. Cl. .......................... 378/19; 378/901
(58) Field of Classification Search .............. 378/4, 378/19, 98.8, 146–154
See application file for complete search history.

(56) References Cited

U.S. PATENT DOCUMENTS

| | | | |
|---|---|---|---|
| 5,473,663 A | 12/1995 | Hsieh | |
| 6,304,625 B1 * | 10/2001 | Senzig | 378/4 |
| 6,529,576 B2 | 3/2003 | Hsieh et al. | |
| 6,625,249 B1 * | 9/2003 | Temkin et al. | 378/4 |
| 6,771,732 B2 * | 8/2004 | Xiao et al. | 378/4 |
| 6,792,077 B2 * | 9/2004 | Rand | 378/149 |
| 6,801,594 B1 | 10/2004 | Ali et al. | |
| 6,856,666 B2 * | 2/2005 | Lonn et al. | 378/8 |
| 7,006,592 B2 | 2/2006 | Ali et al. | |
| 7,106,825 B2 * | 9/2006 | Gregerson et al. | 378/19 |
| 2003/0007604 A1 | 1/2003 | Hsieh et al. | |
| 2003/0185345 A1 | 10/2003 | Hsieh | |
| 2004/0247070 A1 | 12/2004 | Ali et al. | |
| 2005/0100126 A1 | 5/2005 | Mistretta et al. | |
| 2005/0123100 A1 | 6/2005 | Hsieh | |
| 2006/0013357 A1 | 1/2006 | Tang et al. | |
| 2006/0018439 A1 | 1/2006 | Tang et al. | |
| 2006/0227928 A1 * | 10/2006 | Timmer | 378/4 |

* cited by examiner

*Primary Examiner*—Edward J. Glick
*Assistant Examiner*—Irakli Kiknadze
(74) *Attorney, Agent, or Firm*—Carl B. Horton, Esq.; Armstrong Teasdale LLP

(57) ABSTRACT

A method for obtaining data includes scanning an object with radiation to collect projection data using an imaging system having a detector array with detector cells and a post-patient collimator, wherein the post-patient collimator has plates having non-uniform thicknesses. The method further includes applying a correction to the projection data to shift an effective center of at least some of the detector cells to compensate for the non-uniform thicknesses of the collimator plates.

20 Claims, 4 Drawing Sheets

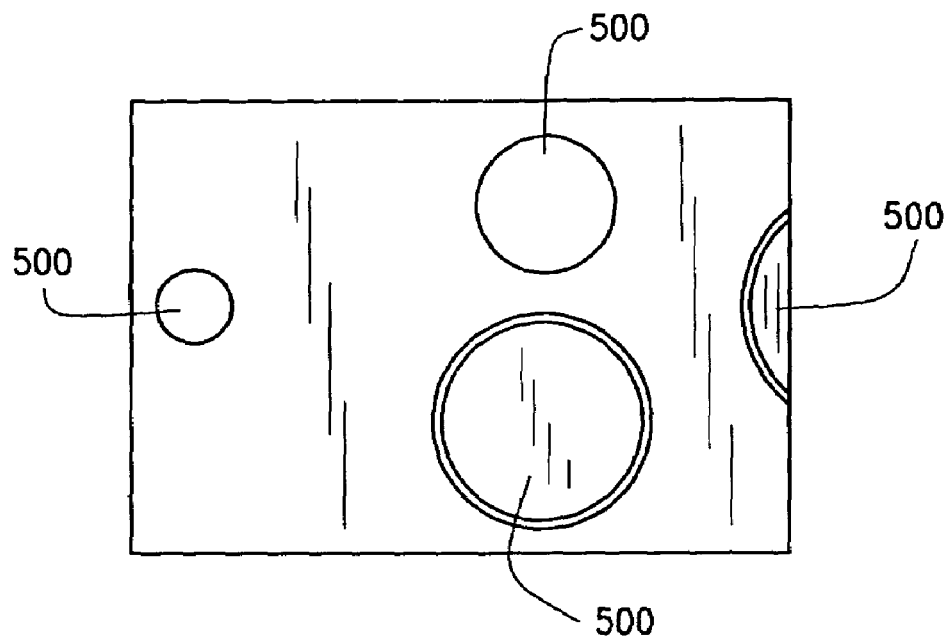
F I G . 5
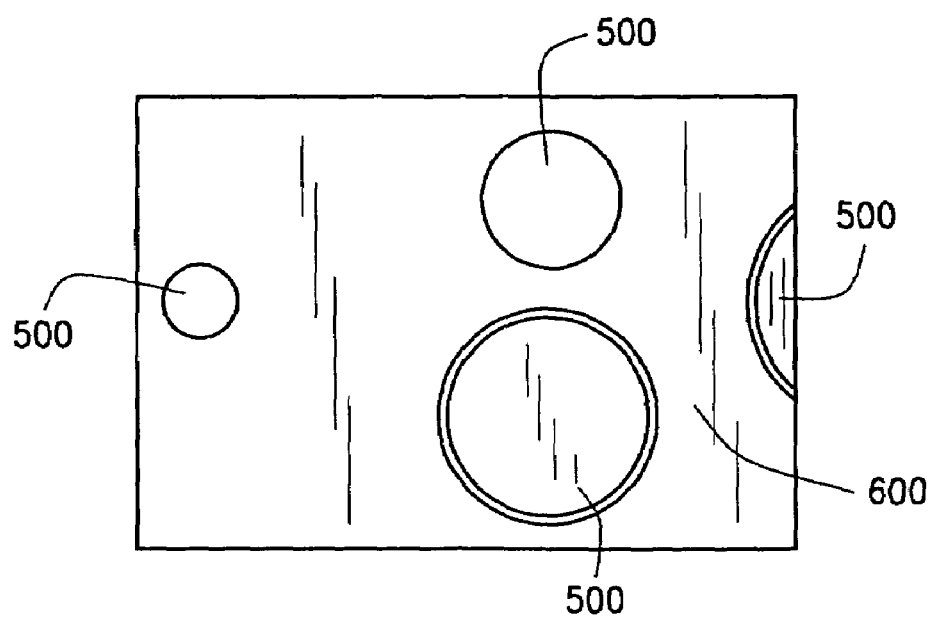
F I G . 6

METHOD AND APPARATUS FOR COMPENSATING NON-UNIFORM DETECTOR COLLIMATOR PLATES

BACKGROUND OF THE INVENTION

This invention relates generally to scanned imaging systems and methods, more particularly to methods and apparatus for reducing artifacts in images obtained from scanning of objects.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

In at least one known third generation CT scanner, a set of post-patient collimator plates is positioned in front of a detector array for scatter rejection. The collimator plates are provided as piece separate from a scintillator pack or module of the detector array. However, providing collimator plates separate from the scintillator pack or modules of the detector array makes it difficult, among other things, to repair and/or replace detector modules. On the other hand, artifacts can occur if collimator plates are supplied as part of each detector module in the detector array, and it is believed that the problem of providing low artifact images using interchangeable detector modules that each include a set of collimator plates has not yet been addressed in the art.

BRIEF DESCRIPTION OF THE INVENTION

One aspect of the present invention therefore provides a method for imaging an object. The scanning is performed by a CT imaging system having a detector array with detector cells and a post-patient collimator, wherein the post-patient collimator has boundary plates between some detector cells and center plates over other detector cells, and boundary plates have a different effective thickness than do the center plates. A correction is applied to the projection data to shift an effective center of at least some of the detector cells to compensate for the non-uniform thickness between the boundary plates and the center plates. An image of the object is then reconstructed using the corrected projection data.

Another aspect of the present invention provides a CT imaging system that includes an x-ray source, a detector array having detector elements or cells, and a post-patient collimator having boundary plates between some detector cells and center plates over other detector cells, and the boundary plates have a different effective thickness than do the center plates. An image processing system is provided that is configured to apply a correction to projection data collected during scanning of an object to thereby shift an effective center of at least some of the detector cells to compensate for the non-uniform thickness between the boundary plates and the center plates, and to reconstruct an image of object using the corrected projection data.

In yet another aspect, the present invention provides a method for obtaining data that includes scanning an object with radiation to collect projection data using an imaging system having a detector array with detector cells and a post-patient collimator, wherein the post-patient collimator has plates having non-uniform thicknesses. The method further includes applying a correction to the projection data to shift an effective center of at least some of the detector cells to compensate for the non-uniform thicknesses of the collimator plates.

In yet another embodiment, additional filtering is performed on the projection data to compensate for the noise difference due to non-uniform collimation plate thickness. The filter is designed such that its parameters change as a function of the detector plate thickness.

It will be appreciated that various configurations of the present invention provide, among other things, an ability to use detector arrays using fully interchangeable detector modules in imaging systems, and that some configurations of the present invention are useful in reducing artifacts in images resulting from non-uniform collimator module plates.

BRIEF DESCRIPTION OF THE DRAWINGS

FIG. 5 is a reconstructed image of simulated cylindrical objects showing the effect of an ideal collimator.

FIG. 6 is a reconstructed image of the simulated cylindrical objects of FIG. 5 showing the artifacts introduced by a collimator having non-uniform plates.

DETAILED DESCRIPTION OF THE INVENTION

A technical effect of some configurations of the present invention is the generation of artifact-free or at least improved images of objects resulting from the detection of radiation passing through an object scanned using a radiation source. Another technical effect of some configurations of the present invention is the ability to utilize fully interchangeable detector modules in an imaging system. These and other technical effects of the present invention will become apparent to one of ordinary skill upon appreciating the subject matter of the present disclosure.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image. Some configurations of the present invention do not necessarily reconstruct an image or generate data representing an image, but do process projection data of an object by compensating the projection data so that and further processing can generate data representing an image and/or produce a viewable image.

Figure 1:
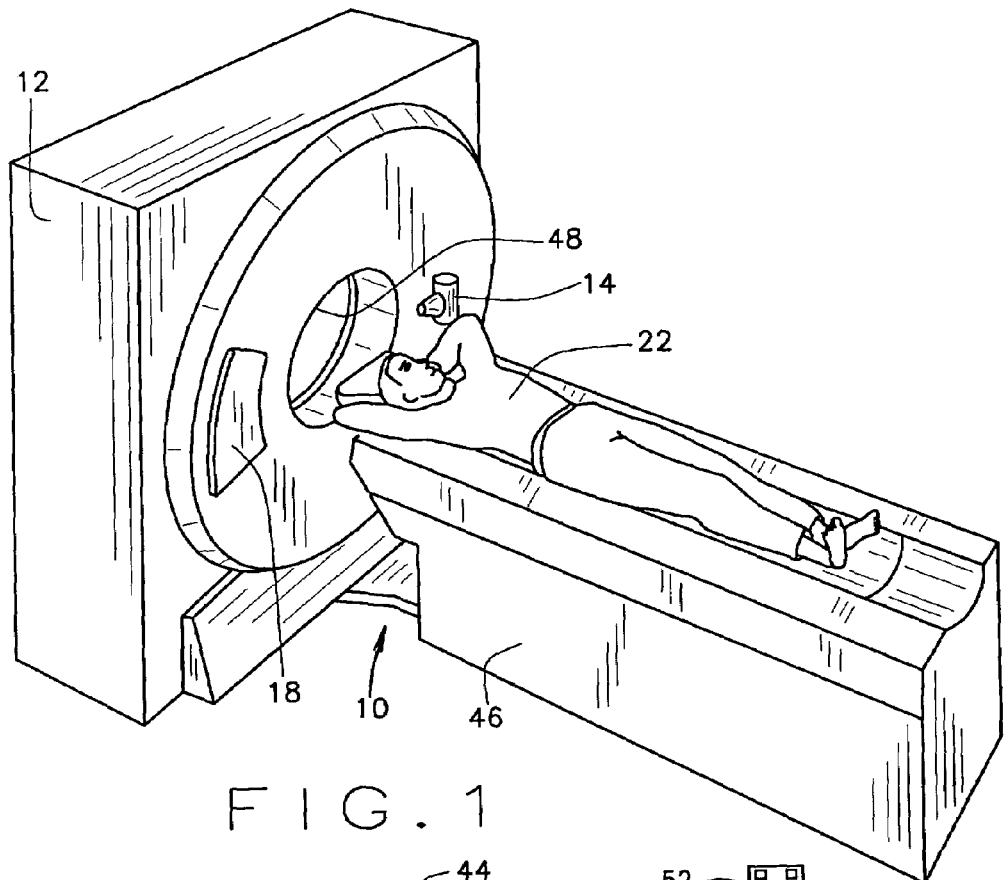
FIG. 1 is a pictorial drawing representative of some configurations of CT imaging apparatus of the present invention.
Figure 2:
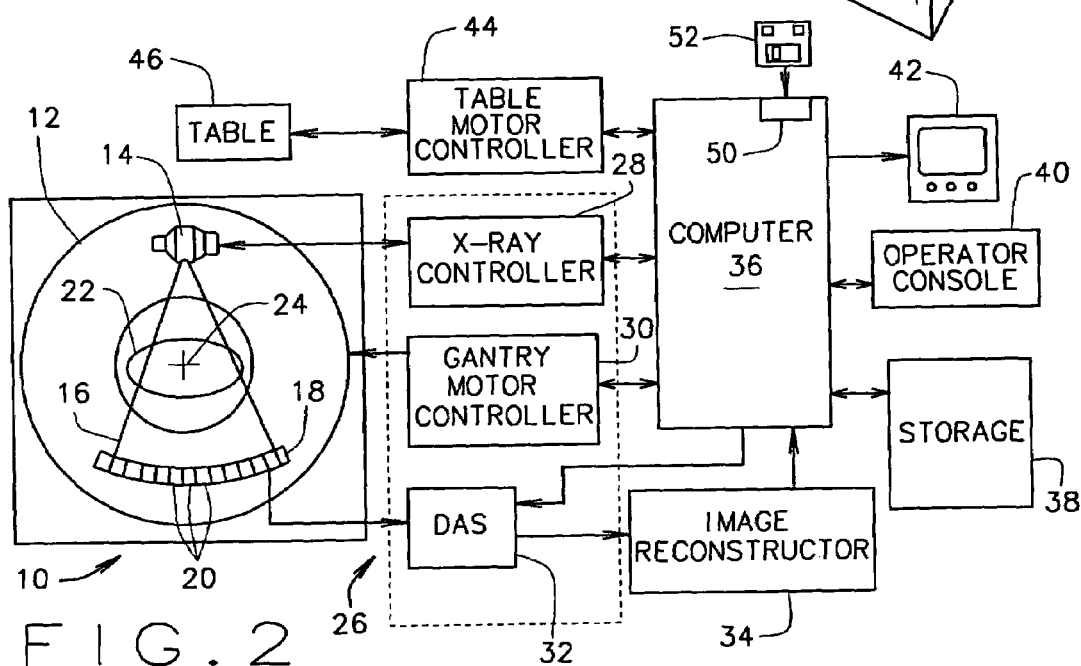
FIG. 2 is a functional block diagram representative of the CT imaging apparatus of FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. Detector array 18 is formed by a plurality of detector rows (not shown) including a plurality of detector elements or cells 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements or cells 20 (i.e., a detector row). However, multi-slice detector array 18 includes a plurality of parallel detector rows of detector elements or cells 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements or cells 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube, liquid crystal, plasma, or any other suitable type of display device 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector—rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

In at least one known third generation CT scanner, a set of post-patient collimator plates is positioned in front of a detector array for scatter rejection. The collimator plates are provided as piece separate from a scintillator pack or module of the detector array. However, providing collimator plates separate from the scintillator pack or modules of the detector array makes it difficult, among other things, to repair and/or replace detector modules.

Figure 3:
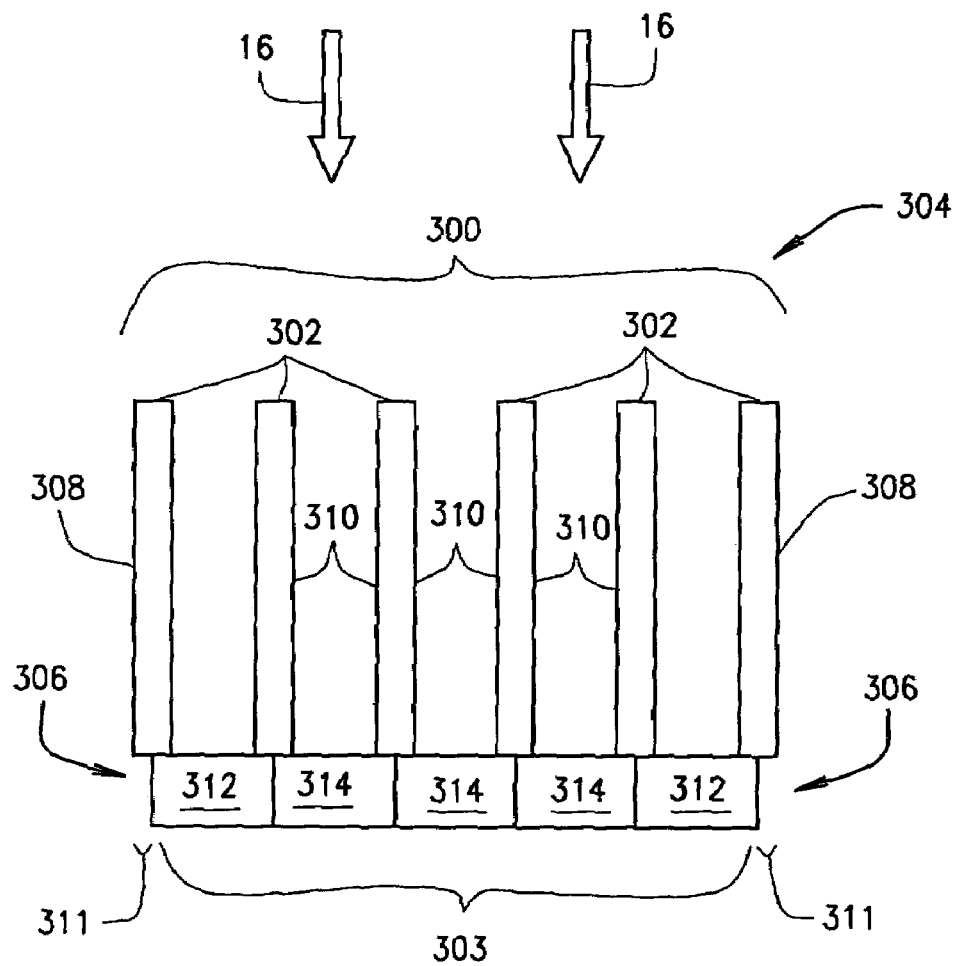
FIG. 3 is a vertical cross-sectional view of a detector module that includes a set of collimator plates.

Referring to FIG. 3, a smaller section 300 of a set of collimator plates 302 (that is, smaller than a set of collimator plates provided separately and placed in front of a plurality of detector modules) can be combined with each individual scintillator module 303 to form a stand-alone detector module 304 entity. However, such a combination results in anomalies at module boundaries or junctions 306 in configurations in which each module 304 includes a separate boundary plate 308 at a junction 306 between two modules 304. If boundary plates 308 are positioned identically to other plates, referred to herein as "center plates" 310, a small gap 311 would occur between adjacent modules 304 at junctions 306 because half the width of boundary plate 308 is positioned over a detector cell 312 and the other half is cantilevered over the edge of detector edge cell 312. The gap would occur because an abutting boundary plate 308 is similarly cantilevered, and thus the detector cell over which it is positioned cannot be made to abut edge cell 312. The resulting gaps would make detector sampling non-uniform and would adversely affecting the detector quarter—quarter offset property. To avoid this problem, boundary collimator plates 308 can be positioned inwardly so that no gap is present between modules 304. This configuration makes the exposure area of a detector edge cell 312 at the module 304 boundaries smaller than the non-boundary cells 314. Without compensation, image artifacts (e.g., streaking artifacts) can result. When the boundary plate 308 thickness is half a center plate 310 thickness, the combined "double plate" is the same thickness as that of a center plate 310, and no artifacts are created from this source. However, as the thicknesses of the boundary plates 308 increase, the amount of degradation increases. (Detector elements or cells 20 in FIG. 2 are all either edge cells 312 or non-boundary cells 314, and there may be scores of modules 304 and many hundreds or thousands of detector elements or cells 20 in a detector array, particularly in the case of a multi-row detector array.)

To control the degradation, thinner boundary plates 308 (less than or equal to half the thickness of center plates 310) could be used at junctions 306. However, thin boundary plates 308 can make the collimator portion of a detector module 304 fragile at its edges. Alternately, a thicker boundary collimator plate 308 at an edge detector cell 312 of one module 304 could be shared by an edge cell 312 of a neighboring detector module 304, i.e., N-cell modules alternate with N+1 plates and N-1 plates, or N-cell modules having N plates can be used in which one edge-cell thicker plate is shared at the boundary of two modules. However, manufacturing complexity is increased when an attempt is made to control degradation using these techniques. Also, more than one detector module type is required, meaning that detector modules 304 are not all interchangeable with one another. In addition, this design makes the repair process of a "field replaceable" detector module more difficult.

Therefore, some configurations of the present invention provide and/or allow thicker boundary plates 308 to be used on all detector modules 304, but provide compensation in image reconstruction that reduces or eliminates the effect of these thicker boundary plates.

Figure 4:
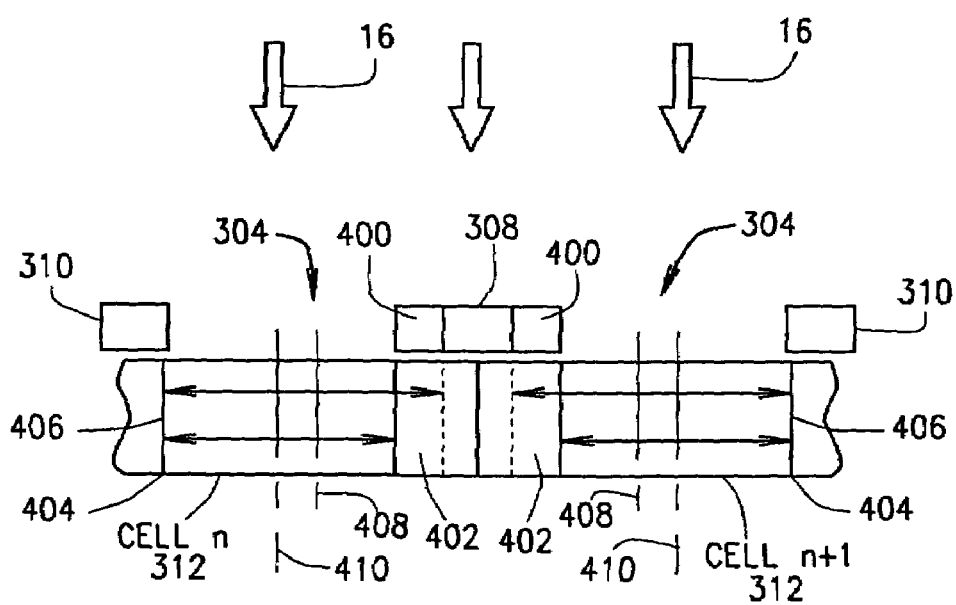
FIG. 4 is a schematic vertical cross-sectional view of a detector module showing the effect of non-uniform collimator plates.

Boundary plates 308 reduce the x-ray flux impinging on a detector and make photon statistics worse for cells 312 at the boundary than for cells 314 in the center. In some configurations and referring to the schematic representation of FIG. 4, central plates 310 represent collimator plates 302 that are placed at the center (i.e., not at an edge) of a detector module 304. Portions 400 of double boundary plate(s) 308 cover portions 402 of boundary cells 312. (Boundary plate 308 in FIG. 4 is shown schematically because FIG. 4 can represent more than one configuration of the present invention. For example, FIG. 4 can represent a configuration in which a single boundary plate 308 of a first detector module 304 is cantilevered over a second, adjacent detector module that does not have a boundary plate on the side adjacent to the first detector module. As another example, FIG. 4 can represent a configuration in which two boundary plates 308, one on each of the adjacent detector modules 304, abut one another.) Also shown in FIG. 4 are exposed areas 404 on detector cells 308 that would result from a nominal collimator plate 302 thickness (i.e., the thickness of a center plate 310) and the smaller, exposed areas 406 that actually result because of the extra thickness of the double plate 308.

A factor that produces image artifacts in configurations such as that shown in FIG. 4 is the size of the actual exposed detector areas 406, and more particularly, a shift of detector cell centers from 408 to 410 caused by the additional plate thickness of double plate 308. Let us denote by t and t' the nominal plate 302 (i.e., center plate 310) thickness and the double boundary plate 308 thicknesses, respectively. The additional plate thickness, $\Delta$, is then simply $\Delta = t'-t$. The amount of shift of the detector cell center, s, is then simply $s=\Delta/4$. The shifting direction is always towards the center of each respective detector module 304. Therefore, the correction is an attempt to interpolate the original samples of at least some of the detector cells 312 so that the interpolated samples represent the detector readings as though the cell center were located at the nominal location 408.

Let us denote by d the spacing between two nominal detector cell centers 408, and let us denote by p(n) and p(n+1) the measured projection readings for two adjacent boundary cells 312, respectively. The spacing between the two adjacent boundary cells 312 (with additional collimation) is then $d+\Delta/2$. Using linear interpolation, corrected projection readings p'(n) and p'(n+1) are:

$$p'(n) = (1-\alpha) \cdot p(n) + \alpha \cdot p(n+1); \text{ and}$$

$$p'(n+1) = \alpha \cdot p(n) + (1-\alpha) \cdot p(n+1); \text{ where}$$

$$\alpha = \frac{\Delta/4}{d + \Delta/2} = \frac{\Delta}{4d + 2\Delta}.$$

Some configurations of the present invention make use of higher order (i.e., nonlinear) interpolations. For example, in some configurations, a fourth order Lagrange interpolation is used. In this interpolation, the coordinates of the measured signals [x1, x2, x3, x4], are [$-3d/2$, $-d/2-\Delta/4$, $d/2+\Delta/4$, $3d/2$]. The interpolated location of the corrected signal, [x2, x3] is [$-d/2$, $d/2$]. An alternative approach is to keep the measured signal and compensate for the location change in the filtering and backprojection steps. The locations of the boundary samples are known and are transmitted to the filtering and backprojection process to compensate for the sample location change. Because the amount of deviation of the boundary cell location is small, the projection sample shift in the filtering process can be ignored and only the deviation in the backprojection process is compensated for.

In an alternative embodiment, compensation for the change during the fan-to-parallel beam rebinning process can be accomplished. That is, assumptions of the original samples being equiangular spaced will no longer be made. The actual location of the boundary samples are input into the fan-parallel rebinning process so that the rebinned parallel samples incorporate the deviation of the boundary samples.

Another impact of the double boundary plates is the difference in the noise of the projection samples of the boundary cells. The area exposed to the x-ray for the center detector cell is d−t, while the boundary cell is d−(t+t')/2. If the input flux to these detectors are the same, the variance of the detected signal for these detectors are proportional to the exposed area. As a result, the boundary cells have slightly higher noise level as compared to the center cell. A method of overcoming this shortcoming is to filter the boundary cells prior to the reconstruction. For example, the final boundary sample can be the weighted sum of the neighboring samples:

$$p'(i, j) = \sum_{n=1}^{1} \sum_{k=1}^{1} w(k, n) p(i+k, j+n)$$

where w(k, n) is the weighting of all cells.

A technical effect of some configurations of the present invention is thus achieved by using a CT imaging system 10 or other scanning imaging system to scan an object 22 to collect projection data. The scanning can be performed by a CT imaging system 10 or other scanning imaging system having a detector array 18 with detector cells 20 and a post-patient collimator 300, wherein the post-patient collimator 300 has boundary plates 308 between some detector cells 312 and center plates 310 over other detector cells 314, and boundary plates 308 have a different effective thickness than do the center plates 310. A correction is applied to the projection data to shift an effective center 410 of at least some of the detector cells to compensate (e.g., by moving the effective center to 408) for the non-uniform thickness between boundary plates 308 and center plates 306. An image of the object is then reconstructed using the corrected projection data. The reconstruction of the image data can be performed using conventional filtering and backprojection.

The collection of projection data in some configurations utilizes, among other things, DAS 32 of CT system 10. Image reconstructor 34, DAS 32, and/or computer 36 are used in some configurations to correct (i.e., compensate) the projection data and/or reconstruct an image of object 22 using the corrected projection data. Image reconstructor 34, DAS 32, and/or computer may be considered as together comprising an image processing system, although this system may comprise these or any other identifiable components that alone or in combination with other components perform the functions required of the image processing system. In some configurations, this image is displayed on display 42, or it may be printed or provided in some other tangible form. Image reconstructor 34, DAS 32, and/or computer 36 may use storage device 38 and/or computer-readable medium 52 for storage of intermediate or final results and/or as a storage medium on which machine-readable instructions are stored that instruct these devices to perform steps of one or more embodiments of the invention. In some configurations, the instructions for performing the correction and the backprojection In some configurations, a CT imaging system 10 is provided that includes an x-ray source 14, a detector array 18 having detector elements or cells 18, and a post-patient collimator 300 having boundary plates 308 between some detector cells 312 and center plates 310 over other detector cells 314, and the boundary plates have a different effective thickness than do the center plates. These configurations also provide an image processing system (for example, image reconstructor 34, DAS 32, and/or computer 36) configured to apply a correction to projection data collected during scanning of an object 22 to thereby shift an effective center 410 of at least some of the detector cells to compensate (e.g., by shifting to 408) for the non-uniform thickness between boundary plates 308 and center plates 310, and to reconstruct an image of object 22 using the corrected projection data.

Configurations of the present invention are not limited solely to CT imaging systems or to detector arrays that comprise a plurality of detector modules. Thus, some configurations of the present invention provide a method for obtaining data that includes scanning an object 22 with radiation 16 to collect projection data using an imaging system 10 having a detector array 18 with a post-patient collimator having non-uniform plate 302 thicknesses. The method further includes applying a correction to the projection data to shift an effective center 410 of at least some of the detector cells 20 to compensate for the non-uniform thickness of the collimator plates.

In a simulation, several cylindrical objects of various densities and sizes were placed inside a scan field of view. To simulate the worst case, most of the cylindrical objects exhibit high-contrast to a water background. FIG. 5 is a reconstructed CT image of these simulated cylindrical objects 500 (ww=40) using an ideal detector array 18. FIG. 6 is a reconstructed CT image of the same objects in which a detector array 18 having "double" boundary plates 308 that are 197 microns thicker than center plates 314. Note the presence of streaking artifacts 600 in FIG. 6.

Figure 7:
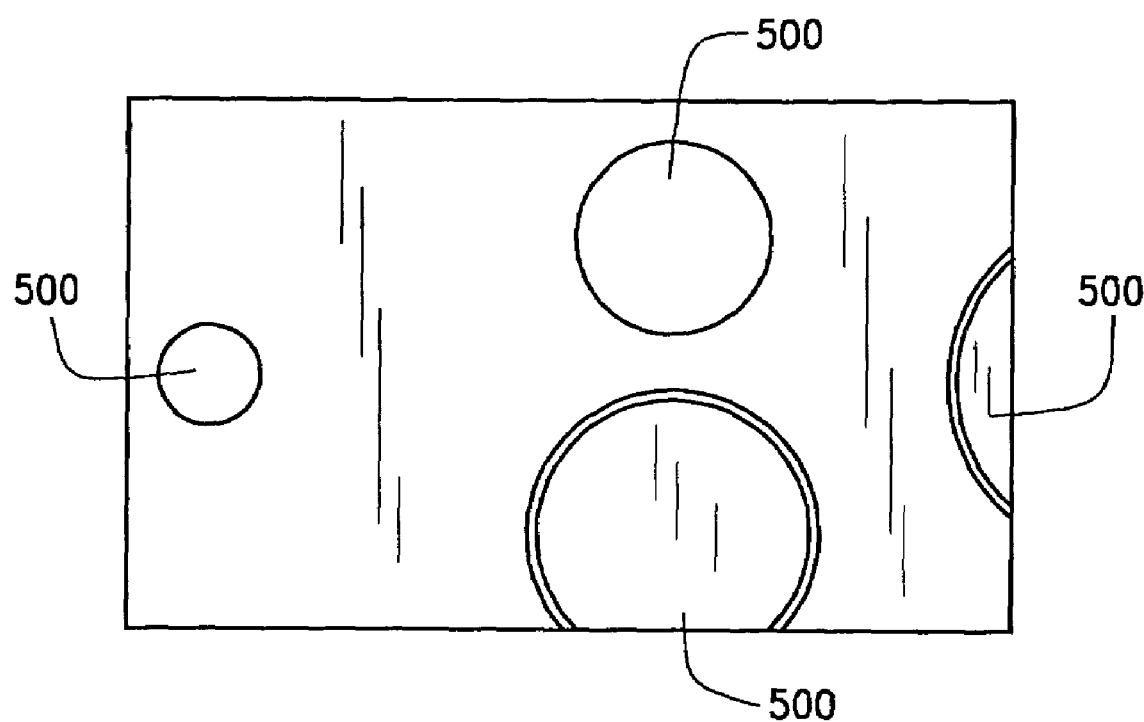
FIG. 7 is a reconstructed image of the simulated cylindrical objects of FIG. 5 showing how the correction applied in some configuration

FIG. 7 is a reconstructed image of the objects using the same simulated detector array 18 as in FIG. 6, but with a fourth-order Lagrange interpolation applied to the simulated projection data. Essentially all artifacts are removed, and the image is all but indistinguishable from the ideal simulation depicted in FIG. 5.

While the invention has been described in terms of various specific embodiments, those skilled in the art will recognize that the invention can be practiced with modification within the spirit and scope of the claims.

What is claimed is:

1. A method for imaging an object, said method comprising:

scanning an object to collect projection data, said scanning performed using a CT imaging system having a detector array with detector cells and a post-patient collimator, wherein the post-patient collimator has boundary plates between some detector cells and center plates over other detector cells, and the boundary plates have a different effective thickness than do the center plates;

obtaining corrected data that compensates for the non-uniform thickness between the boundary plates and the center plates by at least one of applying a correction to the projection data, applying a filtered backprojection process to the projection data, and applying a fan to parallel beam rebinning process to the projection data; and reconstructing an image of the object using the corrected data.

2. A method in accordance with claim 1 further comprising filtering the boundary cells prior to the reconstruction to facilitate reducing noise in the boundary cells relative to the center cell.

3. A method in accordance with claim 1 wherein said applying a correction comprises applying at least one of a linear interpolation and a non-linear interpolation.

4. A method in accordance with claim 3 wherein the non-linear interpolation is a fourth order Lagrange interpolation.

5. A method in accordance with claim 1 wherein the detector array comprises a plurality of modules each having a plurality of detector cells, wherein all of the detector cells are contained in the plurality of modules, and said scanning an object using a CT imaging system comprises scanning the object using a CT imaging system having a detector array in which the plurality of modules are interchangeable with one another.

6. A method in accordance with claim 1 wherein the thicknesses of the boundary plates are twice that of the center plates.

7. A method in accordance with claim 6 wherein said scanning an object comprises scanning the object using a CT imaging system having a detector array with interchangeable detector modules.

8. A method in accordance with claim 7 wherein said applying a correction comprises applying a linear interpolation.

9. A method in accordance with claim 7 wherein said applying a correction comprises applying a non-linear interpolation.

10. A method in accordance with claim 7 wherein the non-linear interpolation is a Lagrange interpolation.

11. A CT imaging system comprising:
an x-ray source;
a detector array having detector cells;
a post-patient collimator having boundary plates between some detector cells and center plates over other detector cells, and the boundary plates have a different effective thickness than do the center plates; and
an image processing system configured to obtain corrected data from projection data collected during scanning of an object by at least one of applying a correction to the projection data, applying a filtered backprojection process to the projection data, and applying a fan to parallel beam rebinning process to the projection data to thereby shift an effective center of at least some of the detector cells to compensate for the nonuniform thickness between the boundary plates and the center plates, and to reconstruct an image of the object using the corrected data.

12. A system in accordance with claim 11 wherein the image processing system is configured to filter the boundary cells prior to the reconstruction to facilitate reducing noise in the boundary cells relative to the center cell.

13. A system in accordance with claim 11 wherein the image processing system is configured to at least one of apply a linear correction and apply a non-linear correction.

14. A system in accordance with claim 11 wherein the image processing system is configured to apply a Lagrange interpolation.

15. A system in accordance with claim 11 wherein the detector array comprises a plurality of modules each having a plurality of detector cells, wherein all of the detector cells are included in the plurality of modules, and the plurality of modules are interchangeable with one another and each module includes a separate set of plates, wherein adjoining plates of different, adjacent modules of the detector array comprise the boundary places and non-adjoining plates of each module comprise the center plates.

16. A system in accordance with claim 11 wherein the thicknesses of the boundary plates are twice that of the center plates.

17. A method for correcting projection data, said method comprising:
scanning an object with radiation to collect the projection data using an imaging system having a detector array with detector cells and a post-patient collimator, wherein the post-patient collimator has non-uniform plate thicknesses, and
correcting the projection data in order to compensate for the non-uniform thickness between the boundary plates and the center plates by at least one of applying a correction to the projection data, applying a filtered backprojection process to the projection data, and applying a fan to parallel beam rebinning process to the projection data.

18. A method in accordance with claim 17 further comprising reconstructing an image of the object using the corrected projection data.

19. A method in accordance with claim 17 further comprising filtering the boundary cells prior to the reconstruction to facilitate reducing noise in the boundary cells relative to the center cell.

20. A method in accordance with claim 17 wherein said applying a correction to the projection data comprises applying at least one of a linear correction and a non-linear correction.

* * * * *